US012213774B1

(12) United States Patent
Aravamudan et al.

(10) Patent No.: US 12,213,774 B1
(45) Date of Patent: Feb. 4, 2025

(54) APPARATUS AND METHOD FOR LOCATING A POSITION OF AN ELECTRODE ON AN ORGAN MODEL

(71) Applicant: nference, Inc., Cambridge, MA (US)

(72) Inventors: Murali Aravamudan, Andover, MA (US); Rakesh Barve, Bengaluru (IN); Suthirth Vaidya, Bengaluru (IN); Uddeshya Upadhyay, Bengaluru (IN); Abhijith Chunduru, Bengaluru (IN); Arjun Puranik, San Jose, CA (US); Sai Saketh Chennamsetty, Bengaluru (IN)

(73) Assignee: nference, Inc., Cambridge, MA (US)

( * ) Notice: Subject to any disclaimer, the term of this patent is extended or adjusted under 35 U.S.C. 154(b) by 0 days.

(21) Appl. No.: 18/402,124

(22) Filed: Jan. 2, 2024

(51) Int. Cl.
*A61B 5/06* (2006.01)
*A61B 8/00* (2006.01)
(Continued)

(52) U.S. Cl.
CPC ............ *A61B 5/066* (2013.01); *A61B 8/0841* (2013.01); *A61B 8/0883* (2013.01); *A61B 8/12* (2013.01);
(Continued)

(58) Field of Classification Search
CPC ...... G16H 50/50; G16H 50/20; A61B 8/0841; A61B 8/0883; A61B 8/12; A61B 8/5261
See application file for complete search history.

(56) References Cited

U.S. PATENT DOCUMENTS

| 4,424,465 A * | 1/1984 | Ohigashi | ............... B06B 1/0622 310/366 |
| 10,828,014 B2 | 11/2020 | Dufour et al. | |

(Continued)

FOREIGN PATENT DOCUMENTS

| CN | 114269272 A * | 4/2022 | ......... A61B 18/1492 |
| CN | 114983476 A * | 9/2022 | ............. A61B 5/015 |

(Continued)

OTHER PUBLICATIONS

A.Ramadani etal.; A survey of catheter tracking concepts and methodologies; Medical Image Analysis; vol. 82, Nov. 2022, 102584.

*Primary Examiner* — Jonathon A. Szumny
(74) *Attorney, Agent, or Firm* — Caldwell Intellectual Property Law

(57) ABSTRACT

An apparatus and method for locating a position of an electrode on an organ model. The apparatus includes a memory communicatively connected to at least a processor, wherein the memory contains instructions configuring the at least a processor to receive an organ model configured to digitally represent an organ, receive a set of sensor data from at least a sensor including an ultrasound sensor, determine an electrode position within the organ model as a function of the set of sensor data using a position machine-learning module, wherein determining the electrode position includes determining a model position within the organ model as a function of the set of sensor data and determining the electrode position within the model position of the organ model as a function of the set of sensor data and add a visual marker onto the electrode position in the model position of the organ model.

16 Claims, 7 Drawing Sheets

(51) Int. Cl.
*A61B 8/08* (2006.01)
*A61B 8/12* (2006.01)
*G16H 50/20* (2018.01)
*G16H 50/50* (2018.01)

(52) U.S. Cl.
CPC .......... *A61B 8/4245* (2013.01); *A61B 8/5261* (2013.01); *G16H 50/20* (2018.01); *G16H 50/50* (2018.01)

(56) References Cited

U.S. PATENT DOCUMENTS

| | | | |
|---|---|---|---|
| 11,445,994 | B2 | 9/2022 | Mansi et al. |
| 2008/0200816 | A1* | 8/2008 | Fujimura ............... A61B 1/042 600/472 |
| 2009/0005679 | A1* | 1/2009 | Dala-Krishna ........... G06T 7/80 600/437 |
| 2012/0215107 | A1* | 8/2012 | Yamamoto .......... G01S 7/52074 600/441 |
| 2017/0188971 | A1* | 7/2017 | Liu ........................ A61B 5/316 |
| 2017/0330075 | A1* | 11/2017 | Tuysuzoglu ............. G06N 7/08 |
| 2019/0200964 | A1* | 7/2019 | Sudhakar ............... A61B 8/461 |
| 2020/0286225 | A1* | 9/2020 | Ben-Haim .............. G06T 19/00 |
| 2021/0236773 | A1* | 8/2021 | Dupont .............. A61B 1/00006 |
| 2021/0282693 | A1* | 9/2021 | Ruppersberg ........ A61B 5/7275 |
| 2021/0303928 | A1* | 9/2021 | Xu ........................ G06T 7/0012 |
| 2022/0142713 | A1* | 5/2022 | Oren .................... A61B 5/6858 |
| 2022/0338939 | A1* | 10/2022 | Ziv-Ari ................. G06N 3/096 |
| 2022/0378292 | A1* | 12/2022 | Ben-Haim .......... A61B 5/6882 |
| 2022/0395213 | A1* | 12/2022 | Jenkins .................. A61B 5/363 |
| 2023/0172635 | A1* | 6/2023 | Bueno .................... A61B 34/10 606/170 |
| 2023/0181087 | A1* | 6/2023 | Rodriguez ............. A61B 5/367 600/523 |
| 2023/0210437 | A1* | 7/2023 | Beeckler ................ A61B 5/367 600/523 |
| 2023/0252064 | A1* | 8/2023 | Ozaki .................... G16H 15/00 707/737 |
| 2023/0293907 | A1* | 9/2023 | Shade ................... A61N 5/1031 600/1 |
| 2023/0397958 | A1* | 12/2023 | Wildeboer ............. A61B 34/20 |
| 2024/0099643 | A1* | 3/2024 | Jenkins .................. A61B 5/287 |
| 2024/0293071 | A1* | 9/2024 | Constantine ........... A61B 5/062 |

FOREIGN PATENT DOCUMENTS

| | | | | |
|---|---|---|---|---|
| EP | 2797516 | B1 * | 11/2016 | ............. A61B 5/015 |
| GB | 2616029 | A * | 8/2023 | .......... A61B 8/0883 |
| KR | 20210149112 | A * | 12/2021 | ............. A61B 8/463 |
| WO | 2020205187 | A1 | 10/2020 | |
| WO | WO-2021099171 | A1 * | 5/2021 | ............. A61B 8/145 |

\* cited by examiner

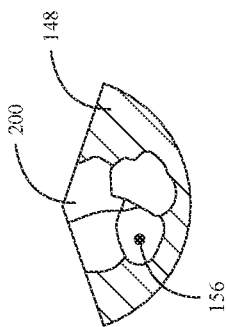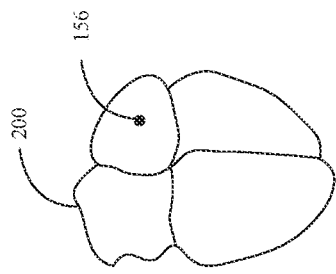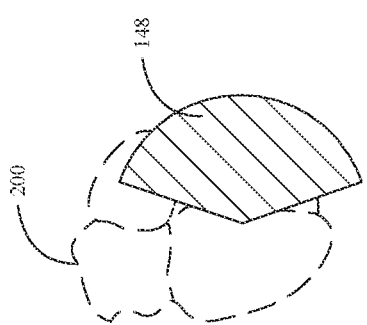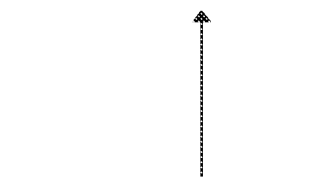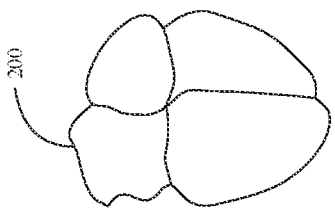
FIG. 2A  FIG. 2B  FIG. 2C  FIG. 2D

APPARATUS AND METHOD FOR LOCATING A POSITION OF AN ELECTRODE ON AN ORGAN MODEL

FIELD OF THE INVENTION

The present invention generally relates to the field of electrode tracking. In particular, the present invention is directed to apparatus and method for locating a position of an electrode on an organ model.

BACKGROUND

Intra-cardiac mapping procedures play a vital role in diagnosing and treating cardiac diseases. Existing solutions often face challenges related to accuracy, latency, and the ability to operate seamlessly in complex anatomical environments. Additionally, magnetic sensors which can be used to locate electrodes are expensive and may be harmful to patient health.

SUMMARY OF THE DISCLOSURE

In an aspect, an apparatus for locating a position of an electrode on an organ model are disclosed. The apparatus includes at least a processor and a memory communicatively connected to the at least a processor, wherein the memory contains instructions configuring the at least a processor to receive an organ model, wherein the organ model is configured to digitally represent an organ, receive a set of sensor data from at least a sensor, wherein the at least a sensor includes an ultrasound sensor, determine an electrode position within the organ model as a function of the set of sensor data using a position machine-learning module, wherein determining the electrode position includes determining a model position within the organ model as a function of the set of sensor data and determining the electrode position within the model position of the organ model as a function of the set of sensor data and add a visual marker onto the electrode position in the model position of the organ model.

In another aspect, method for locating a position of an electrode on an organ model is disclosed. The method includes receiving, using at least a processor, an organ model, wherein the organ model is configured to digitally represent an organ, receiving, using the at least a processor, a set of sensor data from at least a sensor, wherein the at least a sensor includes an ultrasound sensor, determining, using the at least a processor, an electrode position within the organ model as a function of the set of sensor data using a position machine-learning module, wherein determining the electrode position includes determining a model position within the organ model as a function of the set of sensor data and determining the electrode position within the model position of the organ model as a function of the set of sensor data and adding, using the at least a processor, a visual marker onto the electrode position in the model position of the organ model.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIGS. 2A-2D illustrate exemplary embodiments of an organ model;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatuses and methods for locating a position of an electrode on an organ model are disclosed. The apparatus includes at least a processor and a memory communicatively connected to the at least a processor, wherein the memory contains instructions configuring the at least a processor to receive an organ model, wherein the organ model is configured to digitally represent an organ, receive a set of sensor data from at least a sensor, wherein the at least a sensor includes an ultrasound sensor, determine an electrode position within the organ model as a function of the set of sensor data using a position machine-learning module, wherein determining the electrode position includes determining a model position within the organ model as a function of the set of sensor data and determining the electrode position within the model position of the organ model as a function of the set of sensor data and add a visual marker onto the electrode position in the model position of the organ model.

In some embodiments, apparatuses and methods disclosed herein may allow locate a position of an electrode on an organ model without the use of a magnetic sensor. Catheters with magnetic sensors can be guided through the body using external magnetic fields. Magnetic sensors are expensive and may be harmful to patient health. Exemplary embodiments illustrating aspects of the present disclosure are described below in the context of several specific examples.

Figure 1:
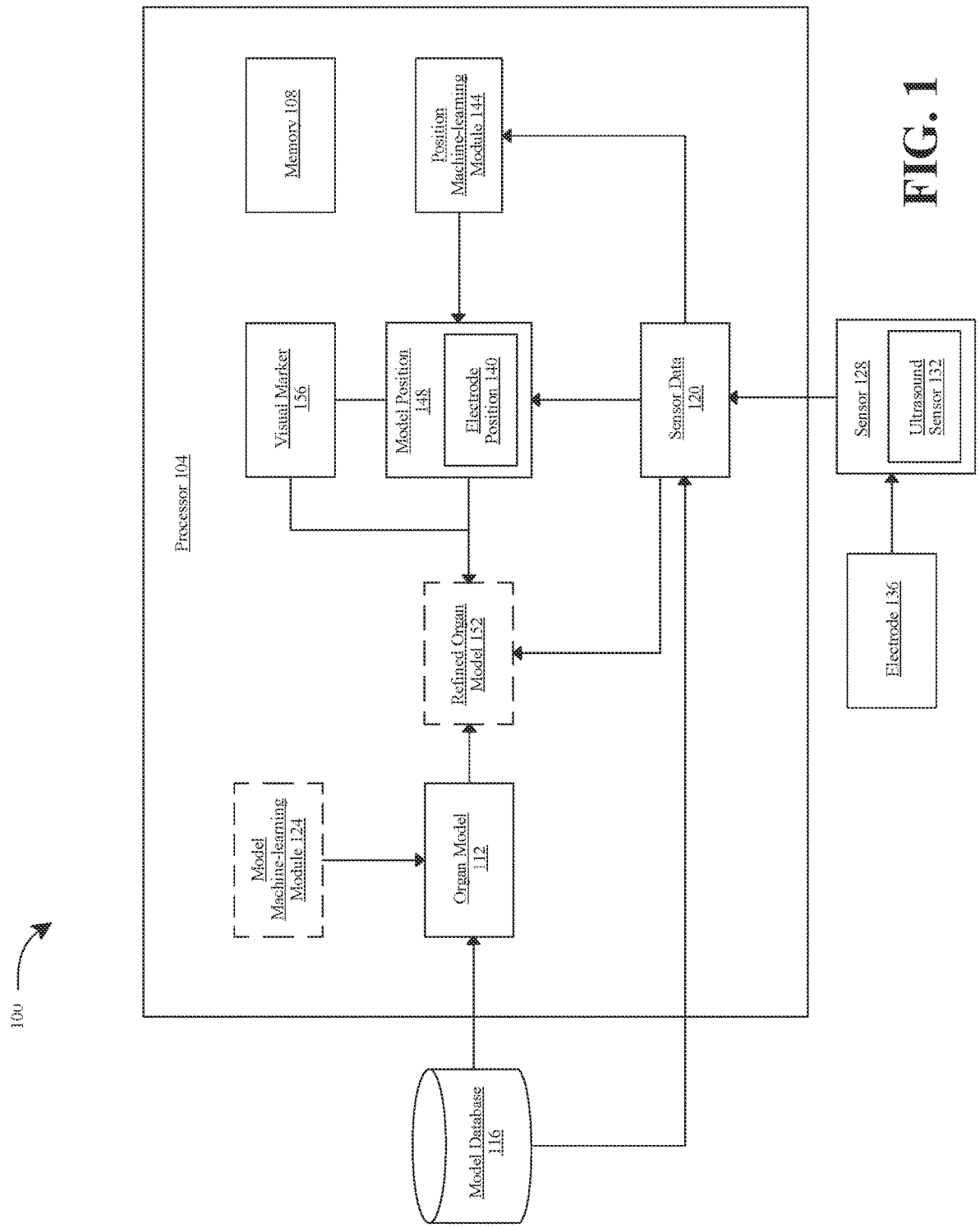
FIG. 1 illustrates a block diagram of an exemplary apparatus for locating position of an electrode on an organ model.

Referring now to FIG. 1, an exemplary embodiment of an apparatus 100 for locating a position of an electrode on an organ model is illustrated. Apparatus 100 includes at least a processor 104. Processor 104 may include, without limitation, any processor described in this disclosure. Processor 104 may be included in a computing device. Processor 104 may include any computing device as described in this disclosure, including without limitation a microcontroller, microprocessor, digital signal processor (DSP) and/or system on a chip (SoC) as described in this disclosure. Processor 104 may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented, as a non-limiting example, using a "shared nothing" architecture.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, apparatus 100 includes a memory 108 communicatively connected to processor 104. For the purposes of this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, memory 108 contains instructions configuring processor 104 to receive an organ model 112. For the purposes of this disclosure, an "organ model" is a digital representation of an organ, capturing its anatomy, geometry, and potentially functional properties. As a non-limiting example, organ model 112 may digitally represent a heart, lung, liver, kidney, pancreas, stomach, intestines, or the like. In some cases, organ model 112 may digitally represent an organ of a human or any individual organism, such as without limitation, a dog, rat, or the like. For the purposes of this disclosure, "digital representation" is the process of expressing information, data, or objects in a form that can be represented using digital technology. As a non-limiting example, organ model 112 may include two-dimensional (2D) model, three-dimensional (3D) model, or the like. In a non-limiting example, organ model 112 may include 3D cardiac model, 3D liver model, or the like. In some embodiments, processor 104 may receive organ model 112 of a human patient or any individual organism, on whom or on which the procedure, study, or otherwise experiment. In some embodiments, processor 104 may receive organ model 112 that includes standard anatomical template. For the purposes of this disclosure, a "standard anatomical template" is a predefined and commonly accepted representation of the human body's anatomical structures. In some cases, a plurality of standard anatomical templates may be selected from model database 116 as described herein based on statistical averages or shared characteristics. In a non-limiting example, organ model 112 may include standard anatomical template selected from a plurality of pre-determined standard anatomical templates. Plurality of pre-determined standard anatomical templates may be generated by processor 104 based on plurality of standard anatomical templates prior to the generation of organ model 112 using 3D reconstruction/modeling algorithms/techniques.

With continued reference to FIG. 1, in some embodiments, processor 104 may be configured to receive organ model 112 from a model database 116. In some embodiments, apparatus 100 may include model database 116. As used in this disclosure, "model database" is a data structure configured to store data associated with an organ model. As a non-limiting example, model database 116 may store organ model 112, electrocardiogram data, metadata, sensor data 120, and the like. In one or more embodiments, model database 116 may include inputted or calculated information and datum related to organ model 112. In some embodiments, a datum history may be stored in model database 116. As a non-limiting example, the datum history may include real-time and/or previous inputted data related to organ model 112. As a non-limiting example, model database 116 may include instructions from a user, who may be an expert user, a past user in embodiments disclosed herein, or the like, where the instructions may include examples of the data related to organ model 112. In a non-limiting example, organ model 112 stored in model database 116 may be obtained from medical organizations. For example, and without limitation, medical organizations may include Mayo Clinic, American Heart Association (AHA), or the like.

With continued reference to FIG. 1, in some embodiments, processor 104 may be communicatively connected with model database 116. For example, and without limitation, in some cases, model database 116 may be local to processor 104. In another example, and without limitation, model database 116 may be remote to processor 104 and communicative with processor 104 by way of one or more networks. The network may include, but is not limited to, a cloud network, a mesh network, and the like. By way of example, a "cloud-based" system can refer to a system which includes software and/or data which is stored, managed, and/or processed on a network of remote servers hosted in the "cloud," e.g., via the Internet, rather than on local severs or personal computers. A "mesh network" as used in this disclosure is a local network topology in which the infrastructure processor 104 connect directly, dynamically, and non-hierarchically to as many other computing devices as possible. A "network topology" as used in this disclosure is an arrangement of elements of a communication network. The network may use an immutable sequential listing to securely store model database 116. An "immutable sequential listing," as used in this disclosure, is a data structure that places data entries in a fixed sequential arrangement, such as a temporal sequence of entries and/or blocks thereof, where the sequential arrangement, once established, cannot be altered or reordered. An immutable sequential listing may be, include and/or implement an immutable ledger, where data entries that have been posted to the immutable sequential listing cannot be altered.

With continued reference to FIG. 1, in some embodiments, model database 116 may include keywords. As used in this disclosure, a "keyword" is an element of word or syntax used to identify and/or match elements to each other. For example, without limitation, keyword may include "cardiac" in the instance that a user or processor 104 is looking for a 3D cardiac model.

With continued reference to FIG. 1, in some embodiments, model database 116 may be implemented, without limitation, as a relational database, a key-value retrieval database such as a NOSQL database, or any other format or structure for use as a database that a person skilled in the art would recognize as suitable upon review of the entirety of this disclosure. Database May alternatively or additionally be implemented using a distributed data storage protocol and/or data structure, such as a distributed hash table or the like. Database may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

With continued reference to FIG. 1, in some embodiments, processor 104 may receive organ model 112 from a remote device. s used in this disclosure "remote device" is an external device to processor 104. For example, and without limitation, remote device may include a computing device, external device, processor, medical device that includes 3D model constructing functions, and the like thereof. For example, and without limitation, remote device may include one or more medical equipment e.g., imaging devices or diagnostic tools. For example, and without limitation, remote device may include smart phone, tablet, laptop, desktop, or the like. In some embodiments, a user may manually input organ model 112 using a remote device. For the purposes of this disclosure, a "user" is any person, groups, or entity that uses an apparatus 100.

With continued reference to FIG. 1, in some embodiments, processor 104 may be configured to construct organ model 112. In some embodiments, processor 104 may receive a set of images of an organ of interest. As used in this disclosure, a "set of images" refers to a collection or group of visual representations captured using any imaging modality or technique described herein. Set of images may include, without limitation, two-dimensional images. In an embodiment, set of images may include a set of intracardiac echocardiography (ICE) images, wherein the "set of ICE images" is a collection of ultrasound images obtained from within organs. In some cases, ICE images may be captured using a specialized catheter equipped with an ultrasound transducer that is inserted into the body and guided to the heart of subject. As a non-limiting example, catheter may include ICE catheter. In an embodiment, set of images may provide a detailed and real-time visualizations of "cardiac anatomy," which refers to the structural composition of the heart and its associated blood vessels. Set of images may also include internal structures, functions, and bold flow patterns of the heart of subject. Other exemplary embodiments of set of images may include, without limitation, X-ray images, magnetic resonance imaging (MRI) scans, computed tomography (CT) scans, ultrasound images, optical images, digital photographs, or any other form of visual data. Additionally, images within set of images may be related in terms of content, time of capture, sequence, or any other relevant parameters described herein. In a non-limiting example, each image of set of images may represent a particular view, angle, or perspective of an object, subject, or scene, and may be in two-dimensional (2D) or 3D format. Images of set of images may include, without limitation, any two-dimensional or three-dimensional images of any anatomy or anatomical structure, including without limitation images of any internal organ, tissue including without limitation muscular, connective tissue, epithelial tissue, and/or nervous tissue, bone, and/or any other element that may be imaged within a human and/or animal body.

Still referring to FIG. 1, as used in this disclosure, a "subject" refers to an individual organism. In an embodiment, subject may include a human, on whom or on which the procedure, study, or otherwise experiment is being conducted. In some cases, subject may include a provider of set of images described herein. In other cases, subject may include a recipient or a participant in a clinical trial or research study. Additionally, or alternatively, subject may include an animal models (i.e., a laboratory rat).

Still referring to FIG. 1, in an embodiment, each ICE image of set of ICE images may include a particular view of subject's heart's chambers, valves, vessel, or any parts of organs thereof. In a non-limiting example, set of images may include multiple views e.g., different angles and perspectives of subject's heart. In another embodiment, set of images may be arranged in a temporal sequence. In a non-limiting example, set of images may include a series of images captured over time, allowing for an observation of dynamic cardiac functions such as beating, blood flow, and/or any organ functions thereof. In some cases, each ICE image of set of images may include a corresponding timestamp, wherein the timestamp may include an indicator showing a date and time of when the corresponding ICE image was taken.

Additionally, or alternatively, and still referring to FIG. 1, various imaging techniques or settings may be applied to set of images that provide specific insights into cardiac anatomy or any organs thereof. In some cases, cardiac anatomy may include a plurality of physical characteristics, spatial relationships, and function aspects of the heart's component; for instance, and without limitation, receiving set of images may include applying a doppler imaging technique, wherein the "doppler imaging technique" is a specialized ultrasound technique used to assess the movement of blood within the body, particularly within the heart and blood vessels. Processor 104 may configure a transducer to send high-frequency sound waves into the subject's body, wherein the sound waves may bounce off moving blood cells and other structures. Reflected waves may then be picked up by the transducer and frequency of the reflected waves changes (Doppler shift) depending on the speed and direction of blood flow may be analyzed to determine one or more blood flow characteristics. In some cases, one or more ICE images within set of images may include visual representations translated based on one or more blood flow characteristics. Such visual representations may be further color-coded, showing the speed and direction of blood flow. As an ordinary person skilled in the art, upon reviewing the entirety of this disclosure, will aware other exemplary modalities of ICE imaging such as, without limitation, computed tomography (CT) scans, magnetic resonance imaging MRI, positron emission tomography (PET) scan, angiography, electrocardiogram (ECG or EKG), single-photon emission computed tomography (SPECT), optical coherence tomography (OCT), thermography, tactile imaging, and/or the like.

With continued reference to FIG. 1, in one or more embodiments, receiving set of images of cardiac anatomy may include receiving a patient profile pertaining to subject. As used in this disclosure, a "patient profile" is a comprehensive collection of information related to an individual patient. In some cases, patient profile may include a variety of different types of data that, when combined, provide a detailed picture of a patient's overall health. In an embodiment, patient profile may include demographic data of patient, for example, and without limitation, patient profile may include basic information about the patient such as name, age, gender, ethnicity, socioeconomic status, and/or the like. In another embodiment, each patient profile may also include a patient's medical history, for example, and without limitation, patient profile may include a detailed record of the patient's past health conditions, medical procedures, hospitalizations, and illnesses such as surgeries, treatments, medications, and/or the like. In another embodiment, each patient profile may include lifestyle Information of patient, for example, and without limitation, patient profile may include details about the patient's diet, exercise habits, smoking and alcohol consumption, and other behaviors that could impact health. In a further embodiment, patient profile may include patient's family history, for example, and without limitation, patient profile may include a record of hereditary diseases. As an ordinary person skilled in the art, upon reviewing the entirety of this disclosure, will be aware of various type of data within patient profiles apparatus 100 may receive and process in consistent with this disclosure.

In a non-limiting example, and still referring to FIG. 1, patient profile may include one or more ICE images or set of images. Receiving set of images may include extracting set of images from patient profile (subsequent to patient identity verification and obtaining consent from subject). In some cases, patient profile of subject may be obtained through hospital information system (HIS) or any other data acquisition platform to securely access patient's electronic medical record (EMR) or other relevant databases. Set of images may be directly or indirectly downloaded or exported. In some cases, each ICE image of set of images may be in a usable and/or computer-readable format such as, without limitation, DICOM format, and necessary metadata (e.g., patient information described above) may be included. Further, receiving set of images may include recording the access and extraction of set of images; for instance, and without limitation, this process may be documented, by processor 104, in the patient's/subject's medical record, databases, or other appropriate logs.

Further, and still referring to FIG. 1, in other embodiments, patient profile may include electrocardiogram (ECG) data. "ECG data," for the purpose of this disclosure, refers to data related to an electrocardiogram of the patient that corresponds to the patient profile. A "electrocardiogram," as described herein, is a medical test that records the electrical activity of subject's heart over a period of time. In an embodiment, ECG data may include one or more recordings captured by a plurality of electrodes placed on patient's skin. In one or more embodiments, ECG data may include information regarding a P wave, T wave, QRS complex, PR interval, ST segment, and/or the like. Processor 104 may associate set of images with ECG data, or in other cases, receiving set of images may include receiving ECG data pertaining to subject associated with set of images. Such ECG data may be collected simultaneously during ICE imaging. In some cases, set of images may be linked with ECG data by one or more unique identifiers, such as without limitations, timestamps or other metadata described herein. In a non-limiting example, ECG data may be used to identify specific cardiac events or phases of the cardiac cycle, and the corresponding ICE images may be analyzed to see how heart's structure changes during those times. In some embodiments, processor 104 may receive a set of images, patient profile or ECG data from model database 116, remote device, or the like. In some embodiments, a user may manually input a set of images, patient profile or ECG data.

With continued reference to FIG. 1, processor 104 may be configured to generate a 3D organ model as a function of set of images of organs. In a non-limiting example, 3D organ model may include a 3D voxel occupancy representation (VOR). As used in this disclosure, a "3D voxel occupancy representation (VOR)" of an organ is a 3D digital representation of a spatial structure of the organ, wherein the representation is composed of a plurality of discrete volumetric elements known as voxels. A "voxel," for the purpose of this disclosure, is a 3D equivalent of a pixel in 2D imaging. While a pixel represents a point in a 2D image and may include properties such as color and/or brightness, a voxel may represent a volume in a 3D space and may include additional properties such density/occupancy as described below. In an embodiment, each voxel of plurality of voxels within 3D VOR may represent a specific portion of cardiac anatomy. In some cases, voxel may be a smallest distinguishable box-shaped part (i.e., 1px·1px·1px) of a three-dimensional image. In some cases, each voxel of plurality of voxels within VOR may be represented as a cube or rectangular prism (although other shapes may be used in specialized applications). Each voxel may include a size that determines a resolution of the 3D image or model. In an embodiment, smaller voxels may provide higher resolution; however, it may require more computational resources (e.g., RAM) for processor 104 to process.

In an embodiment, and still referring to FIG. 1, each voxel of plurality of voxels within VOR may include one or more embedded values. As used herein, "embedded values" refers to specific numerical or categorical data associated with each voxel. In some cases, embedded values may represent various attributes or characteristics of the corresponding portion of cardiac anatomy that voxel represents. In a non-limiting example, embedded values may include density values, intensity values, texture information, or any other quantitative measures that provide insights into the underlying cardiac tissue. Such embedded values may be derived from set of ICE images or other imaging modalities used to generate organ model 112. In some cases, embedded values may be utilized, by processor 104, to differentiate between different types of cardiac tissues, such as myocardial tissue, blood vessels, or chambers. Embedded values may also facilitate the visualization of dynamic cardiac functions, for example, and without limitation, blood flow or heart beating by encoding temporal information such as timestamps within plurality of voxels.

In some cases, and still reference to FIG. 1, one or more embedded values, such as, without limitations, occupancy or density, may be derived from set of images described herein by processor 104. In a non-limiting example, determining occupancy status of each voxel of plurality of voxels may include converting set of ICE images to a set of binary images and determining occupancy status of each voxel as a function of the structure of interest's binary value. In some cases, occupancy status may include a value representing the likelihood of occupancy of the corresponding heart tissue. In another non-limiting example, density may be calculated, by processor 104, for each voxel as a function of the echogenicity of one or more pixels on a given ICE image, wherein, the brightness of the given ICE image may be analyzed since different tissues reflect ultrasound waves differently.

With continued reference to FIG. 1, generating 3D organ model may include generating a 3D array. In some cases, processor 104 may divide 3D space into a grid of plurality of voxels, each with specific x, y, and z coordinates as embedded values. Each element of 3D array may correspond to a voxel. In some cases, 3D array may allow for easy access and manipulation of plurality of voxels, enabling various analyses, visualizations, and transformations either described or not described herein. In a non-limiting example, embedded values may include a density of the tissue at a specific location of a patient's body derived from one or more ICE images of set of images.

In yet another embodiment, and still referring to FIG. 1, cells may be continuous, meaning that one or more cells may represent one or more continuous regions of space rather than discrete, separate units. In a non-limiting example, instead of being uniform, mapped presence indicator and/or other embedded values may vary continuously across different cells or cell's volume. In such embodiment, processor 104 may use interpolation to estimate other (unknown) embedded values within a range based on existing values such as known embedded values at specific points, thereby allowing for smooth transitions between cells. Exemplary interpolation methods may include, without limitation, linear interpolation, cubic interpolation, and/or the like. For example, and without limitation, if the corners of a cell have known values interpolation can be used to estimate the values at any point within the cell based on those corner values.

In a non-limiting example, and still referring to FIG. 1, 3D organ model may include a 3D grid having a plurality of cells e.g., voxels, wherein each cell may contain a continuous range of values representing tissue density, blood flow velocity, or other properties (i.e., embedded values). Processor 104 may be configured to apply trilinear or tri-cubic interpolation to estimate tissue density within each cell based on presence indicator or other known values at the cell's boundaries, since tissue densities change gradually; such 3D grid may provide a smooth, continuous representation of heat's internal structures, allowing for more nuanced analysis and visualization as described below. In a further embodiment, 3D grid with continuous cells may be additionally used in fluid dynamics simulations.

With continued reference to FIG. 1, in some embodiments, 3D grid may include one or more spatial features extracted from set of images of cardiac anatomy. As used in this disclosure, "spatial features" are specific characteristics or attributes related to the spatial arrangement, shape, size, texture, or orientation of structures within a 3D space. In some cases, spatial features may include one or more embedded values described herein and their combinations thereof. In a non-limiting example, spatial feature may be represented numerically as a vector, a metric or other mathematical constructs that capture specific spatial characteristics. In some cases, spatial features may also be visualized as contours, surfaces, or other geometric representations. In an embodiment, spatial features may be extracted using edge detection, texture analysis, or other image processing techniques (e.g., cleaning and enhancing images, image segmentation, and/or the like). In another embodiment, one or more machine-learning models, such as convolutional neural networks (CNNs), may be used to extract complex spatial features.

Still referring to FIG. 1, as used in this disclosure, a "vector" is a data structure that represents one or more a quantitative values and/or measures of one or more spatial features. A vector may be represented as an n-tuple of values, where n is one or more values, as described in further detail below; a vector may alternatively or additionally be represented as an element of a vector space, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent, for instance as measured using cosine similarity as computed using a dot product of two vectors; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm: , where $a_i$ is attribute number i of the vector. Scaling and/or normalization may function to make vector comparison independent of absolute quantities of attributes, while preserving any dependency on similarity of attributes.

Still referring to FIG. 1, in a non-limiting example, one or more spatial features may include one or more shape features (i.e., characteristics related to the shape of specific organ structures), such as curvature, surface area, volume, and/or the like. In another non-limiting example, one or more spatial features may include one or more texture features (i.e., characteristics related to the texture or pattern within tissues, as seen set of images), such as without limitation gray-level co-occurrence matrix (GLCM) features representing the texture of heart muscle tissue. In another non-limiting example, one or more spatial features may include one or more orientation features (i.e., characteristics related to the orientation or alignment of organ structures), such as without limitation the angle or alignment of the septum within the heart. In a further non-limiting example, one or more spatial features may include one or more edge and boundary features (i.e., characteristics related to the edges or boundaries between different organ structures or tissues), such as without limitation edge detection features highlighting the boundary between the myocardium and the cardiac chambers. As an ordinary person skilled in the art, upon reviewing the entirety of this disclosure, will be aware of various spatial features extracted from set of images in consistent with this disclosure.

With continued reference to FIG. 1, in some embodiments, apparatus 100 may include a computer vision model configured to generate 3D organ model. A "computer vision model," for the purpose of this disclosure, is a computation model designed to interpret and make determinations based on visual data. In an embodiment, computer vision model may process set of images, to make a determination about a scene, space, and/or object related to an organ. In a non-limiting example, computer vision model may be used for registration of plurality of voxels within a 3D space. In some cases, registration may include image processing described herein, such as without limitation object recognition, feature detection, edge/corner detection, and the like. Non-limiting example of feature detection may include scale invariant feature transform (SIFT), Canny edge detection, Shi Tomasi corner detection, and the like. In some cases, registration may include one or more transformations to orient an ICE image relative a 3D coordinate system; exemplary transformations include without limitation homography transforms and affine transforms. In an embodiment, registration of ICE image to a coordinate system may be verified and/or corrected using object identification and/or computer vision, as described above. For instance, and without limitation, an initial registration to two dimensions, represented for instance as registration to the x and y coordinates, may be performed using a two-dimensional projection of points in three dimensions onto the ICE image; however, a third dimension of registration, representing depth and/or a z axis, may be detected by utilizing depth-sensing techniques such as Doppler imaging. Alternatively, the third dimension may be inferred from the known geometry and orientation of the imaging device (e.g., ICE catheter), or through the application of one or more machine-learning models trained to interpret depth from the two-dimensional projection.

With continued reference to FIG. 1, in some embodiments, processor 104 may generate or construct organ model 112 using a model machine-learning module 124. Model machine-learning module 124 disclosed herein may be consistent with machine-learning module described with respect to FIG. 3. In some embodiments, processor 104 may use a model machine-learning module 124 to implement one or more algorithms or generate one or more model machine-learning models. As a non-limiting example, model machine-learning module 124 may include cardiac model, liver model, pancreas model, intestine model machine-learning model, or the like. In some embodiments, processor 104 may be configured to determine one model machine-learning model from a plurality of model machine-learning models of model machine-learning module 124. For example, and without limitation, processor 104 may determine a cardiac model machine-learning model from a plurality of model machine-learning models of model machine-learning module 124 to generate a cardiac organ model. For the purposes of this disclosure, a "cardiac model machine-learning model" is a machine-learning model that generates an organ model for a cardiac anatomy. In some embodiments, processor 104 may determine one model machine-learning model from a plurality of model machine-learning models of model machine-learning module 124 as a function of sensor data 120, ECG data, or the like. In a non-limiting example, processor 104 may determine a cardiac model machine-learning model from a plurality of model machine-learning models of model machine-learning module 124 to generate a cardiac organ model as processor 104 receives ECG data. In another non-limiting example, processor 104 may determine a liver model machine-learning model from a plurality of model machine-learning models of model machine-learning module 124 to generate a liver organ model as processor 104 receives sensor data 120 that includes a set of images related to liver. Model machine-learning module 124 is exemplary and may not be necessary to generate one or more model machine-learning models and perform any machine-learning described herein.

With continued reference to FIG. 1, processor 104 may be configured to generate model training data. In one or more embodiments, one or more model machine-learning models may be generated using model training data. Model training data may include inputs and corresponding predetermined outputs so that a model machine-learning model may use correlations between the provided exemplary inputs and outputs to develop an algorithm and/or relationship that then allows model machine-learning model to determine its own outputs for inputs. Model training data may contain correlations that a machine-learning process may use to model relationships between two or more categories of data elements. For example, and without limitation, model training data may include correlations between exemplary patient profile, ECG data, or set of images and exemplary organ models. In a non-limiting example, processor 104 may generate cardiac model training data, wherein the cardiac model training data may include exemplary electrocardiogram data as input and a plurality of cardiac models as output, train a cardiac model machine-learning model of a plurality of model machine-learning models of a model machine-learning module 124 using cardiac model training data and construct a three-dimensional cardiac model of organ model 112 as a function of ECG data using a trained cardiac model machine-learning model of a plurality of model machine-learning models of a model machine-learning module 124. For example, and without limitation, model training data may include correlation between ECG data and cardiac organ model. This is an exemplary case when a cardiac model machine-learning model is determined to generate an organ model 112; in other cases, various model machine-learning models may be used to generate different organs models 112.

With continued reference to FIG. 1, exemplary inputs and outputs may come from a database, such as any database described in this disclosure, or be provided by a user. In other embodiments, a model machine-learning module 124 may obtain a training set by querying a communicatively connected database that includes past inputs and outputs. Model training data may include inputs from various types of databases, resources, and/or user inputs and outputs correlated to each of those inputs so that a model machine-learning model may determine an output. Correlations may indicate causative and/or predictive links between data, which may be modeled as relationships, such as mathematical relationships, by model machine-learning models. In one or more embodiments, model training data may be formatted and/or organized by categories of data elements by, for example, associating data elements with one or more descriptors corresponding to categories of data elements. As a non-limiting example, model training data may include data entered in standardized forms by persons or processes, such that entry of a given data element in a given field in a form may be mapped to one or more descriptors of categories. Elements in model training data may be linked to descriptors of categories by tags, tokens, or other data elements. In a further embodiment, training data may include previous outputs such that one or more model machine-learning models iteratively produces outputs. In some embodiments, model training data may be iteratively updated through a feedback loop. As a non-limiting example, model training data may be iteratively updated as a function of newly collected set of images, patient profile, ECG data, organ models, or the like.

Still referring to FIG. 1, model machine-learning module 124 may be used to generate model machine-learning model and/or any other model machine-learning models using model training data. Model machine-learning model may be trained by correlated inputs and outputs of model training data. Model training data may include data sets that have already been converted from raw data whether manually, by machine, or any other method. In an embodiment, generating organ model 112 may include receiving cardiac model training data, wherein the cardiac model training data may include a plurality of image sets as input and a plurality of computed tomography (CT) based cardiac anatomy models as output, and wherein each image set of plurality of image sets may include any images described in this disclosure. In some cases, cardiac model training data may be received from model database 116 or other databases. In other cases, cardiac model training data may be collected by a data acquisition unit from external sources such as one or more medical equipment's e.g., imaging devices or diagnostic tools, wherein the data acquisition may be configured as an intermediary between the data source and model machine-learning module 124.

Still referring to FIG. 1, as used in this disclosure, a "computed tomography (CT) based cardiac anatomy model" refers to a 3D representation of the heart and surrounding structures that is created using data from CT scans. Computed Tomography is a medical imaging technique that uses X-rays to capture cross-sectional images (slices) of the body. By taking a plurality of slices, a CT scan creates a detailed 3D representation of the internal structure. In an embodiment, CT-based cardiac anatomy model may include 3D representations of the heart including chambers, valves, blood vessels, and surrounding tissues. In some cases, CT-based cardiac anatomy model may be interactive; for instance, medical professionals may rotate, zoom, and/or explore CT-based cardiac anatomy model from various angles. In some cases, plurality of CT-based cardiac anatomy models may be generated prior to the training of the cardiac machine-learning model. Plurality of CT-based cardiac anatomy models may be generated using existing techniques in the field as described above such as, without limitation, FAM, cardiac CT merging, among others. In a non-limiting example, plurality of CT-based cardiac anatomy models may provide ground through or references models against cardiac machine-learning model that is being trained. In a non-limiting example, generating organ model 112 of cardiac anatomy further includes training cardiac machine-learning model using cardiac anatomy training data described herein. Cardiac machine-learning model trained using cardiac model training data may be able to interpret ICE images by learning relationships between ICE images and corresponding CT-based cardiac anatomy models. Processor 104 is further configured to generate organ model 112 of cardiac anatomy as a function of set of images using trained cardiac machine-learning model. In some cases, organ model 112 e.g., 3D VOR may be interpreted, visualized, and analyzed by processor 104 in similar manner to CT-based cardiac anatomy models, wherein both are 3D structures that correspond to ICE images.

With continued reference to FIG. 1, in an embodiment, cardiac anatomy modeling model may include a deep neural network (DNN). As used in this disclosure, a "deep neural network" is defined as a neural network with two or more hidden layers. Neural network is described in further detail below with reference to FIGS. 4-5. In a non-limiting example, cardiac anatomy modeling model may include a convolutional neural network (CNN). Generating 3D organ model of cardiac anatomy may include training CNN using cardiac anatomy training data and generating 3D organ model as a function of set of images using trained CNN. A "convolutional neural network," for the purpose of this disclosure, is a neural network in which at least one hidden layer is a convolutional layer that convolves inputs to that layer with a subset of inputs known as a "kernel," along with one or more additional layers such as pooling layers, fully connected layers, and the like. In some cases, CNN may include, without limitation, a deep neural network (DNN) extension. Mathematical (or convolution) operations performed in the convolutional layer may include convolution of two or more functions, where the kernel may be applied to input data e.g., set of images through a sliding window approach. In some cases, convolution operations may enable processor 104 to detect local/global patterns, edges, textures, and any other spatial features described herein within each ICE image of set of images. Spatial features may be passed through one or more activation functions, such as without limitation, Rectified Linear Unit (ReLU), to introduce non-linearities into the processing step of generating 3D organ model of cardiac anatomy. Additionally, or alternatively, CNN may also include one or more pooling layers, wherein each pooling layer is configured to reduce the dimensionality of input data while preserving essential features within the input data. In a non-limiting example, CNN may include one or more pooling layer configured to reduce the spatial dimensions of spatial feature maps by applying downsampling, such as max-pooling or average pooling, to small, non-overlapping regions of one or more spatial features.

Still referring to FIG. 1, CNN may further include one or more fully connected layers configured to combine spatial features extracted by the convolutional and pooling layers as described above. In some cases, one or more fully connected layers may allow for higher-level pattern recognition. In a non-limiting example, one or more fully connected layers may connect every neuron (i.e., node) in its input to every neuron in its output, functioning as a traditional feedforward neural network layer. In some cases, one or more fully connected layers may be used at the end of CNN to perform high-level reasoning and produce the final output such as, without limitation, a 3D organ model of cardiac anatomy. Further, each fully connected layer may be followed by one or more dropout layers configured to prevent overfitting, and one or more normalization layers to stabilize the learning process described herein.

With continued reference to FIG. 1, CNN may further include a 3D CNN, wherein the 3D CNN, unlike standard 2D CNN, may include utilization of one or more 3D convolutions which allow them to directly process 3D data, thereby enabling processor 104 to generate 3D structures such as 3D organ model of cardiac anatomy using the 3D CNN. In a non-limiting example, 3D CNN may include one or more 3D filters (i.e., kernels) that move through the set of images in three dimensions and capturing spatial relationships in x, y, and z axis. Similar to 3D convolutions, 3D CNN may further include one or more 3D pooling layers that may be used to reduce the dimensionality of ICE images while preserving spatial features as described above. Additionally, or alternatively, an encoder-decoder structure may be implemented (extended to 3D), by processor 104, in 3D CNN, wherein the encoder-decoder structure includes an encoding path that captures the context and a decoding path that enables precise localization in a same manner as U-net as described above. Such encoder-decoder structures may also include a plurality of skip connections, allowing 3D CNN to use information from multiple resolutions to improve the process of generating 3D organ model of cardiac anatomy.

With continued reference to FIG. 1, in an embodiment, training a cardiac machine-learning model (i.e., CNN) may include selecting a suitable loss function to guide the training process. In a non-limiting example, a loss function that measures the difference between the predicted 3D VORs and the ground truth 3D structure e.g., CT-based cardiac anatomy models may be used, such as, without limitation, mean squared error (MSE) or a custom loss function may be designed for one or more embodiments described herein. Additionally, or alternatively, optimization algorithms, such as stochastic gradient descent (SGD), may then be used to adjust the cardiac anatomy modeling model's parameters to minimize such loss. In a further non-limiting embodiment, instead of directly predicting 3D organ model, cardiac machine-learning model may be trained as a regression model to predict presence indicators 136 and/or other embedded values described herein for each voxel of plurality of voxels within a 3D grid. Additionally, CNN may be extended with additional deep learning techniques, such as recurrent neural networks (RNNs) or attention mechanism, to capture additional features and/or data relationships within input data. These extensions may further enhance the accuracy and robustness of the cardiac anatomy modeling.

With continued reference to FIG. 1, processor 104 may be configured to generate an organ model 112 of cardiac anatomy. In some cases, organ model 112 may be generated through a direct 3D reconstruction from a series of (2D) ICE images. In a non-limiting example, set of images may include a plurality of ICE images captured from different angles and positions within the heart. Processor 104 may be configured to apply one or more 3D reconstruction algorithms, such as without limitation, marching cubes, contour detection and segmentation, active contour models, and/or the like to create a coherent 3D representation (organ model 112). In some cases, such direct 3D reconstruction may leverage the inherent spatial information within set of images, providing a direct and intuitive way to model the organ model 112. In a further embodiment, generic 3D modeling techniques may be applied to create the 3D model. In some cases, generic 3D modeling techniques may include surface modeling, solid modeling, or parametric modeling, among others. As an ordinary person skilled in the art, upon reviewing the entirety of this disclosure, will be aware of various 3D reconstruction algorithms may be used by processor 104 to generate organ model 112. In some embodiments, organ model 112 may provide a 'starting point' for refinement and customization, allowing for the incorporation of more detailed and patient-specific information as further described in detail below.

Additionally, or alternatively, and still referring to FIG. 1, organ model 112 may be generated based on a plurality of standard anatomical templates. In an embodiment, generating organ model 112 may include selecting model machine-learning model from plurality of model machine-learning models based on set of ICE images. In some cases, model machine-learning model may represent a typical or average cardiac anatomy that is most similar to cardiac anatomy pertaining to subject. Such similarity may be determined based on one or more similarity metrics, such as without limitation, structural similarity index (SSI), MSE, peak signal-to-noise ratio (PSNR), normalized cross-correlation (NCC), Pearson correlation coefficient, and/or the like between set of images and each image sets stored in model database 116. Model machine-learning model may be adjusted and customized to fit the specific patient's ICE images. Processor 104 may be configured to apply one or more 3D reconstruction algorithms, such as without limitation, marching cubes, contour detection and segmentation, active contour models, and/or the like to create a coherent 3D representation e.g., organ model 112. In a further embodiment, generic 3D modeling techniques may be applied to create organ model 112. In some cases, generic 3D modeling techniques may include surface modeling, solid modeling, or parametric modeling, among others. As an ordinary person skilled in the art, upon reviewing the entirety of this disclosure, will be aware of various 3D reconstruction algorithms may be used by processor 104 to generate organ model 112.

With continued reference to FIG. 1, memory 108 contains instructions configuring processor 104 to receive a set of sensor data 120 from at least a sensor 128. For the purposes of this disclosure, a "sensor" is a device that produces an output signal for the purpose of sensing a physical phenomenon. For example, and without limitation, sensor 128 may transduce a detected phenomenon, such as without limitation, temperature, voltage, current, pressure, speed, motion, light, moisture, sound waves, and the like, into a sensed signal. Sensor 128 may output the sensed signal. Sensor 128 may include any computing device as described in the entirety of this disclosure and configured to convert and/or translate a plurality of signals detected into electrical signals for further analysis and/or manipulation. Electrical signals may include analog signals, digital signals, periodic or aperiodic signal, step signals, unit impulse signal, unit ramp signal, unit parabolic signal, signum function, exponential signal, rectangular signal, triangular signal, sinusoidal signal, sinc function, or pulse width modulated signal. Any datum captured by sensor 128 may include circuitry, computing devices, electronic components or a combination thereof that translates into at least an electronic signal configured to be transmitted to another electronic component. In a non-limiting embodiment, sensor 128 may include a plurality of sensors included in a sensor suite. In one or more embodiments, and without limitation, sensor 128 may include a plurality of sensors 128. Sensor 128 includes an ultrasound sensor 132. For the purposes of this disclosure, an "ultrasound sensor" is a device that uses ultrasonic waves. In a non-limiting example, ultrasound sensor 132 may measure the distance to an object using ultrasonic sound waves. In some embodiments, ultrasound sensor 132 may include an electrode 136. For the purposes of this disclosure, an "electrode" is a conductive material or element that facilitates the transmission and reception of electrical signals associated with ultrasound waves. In a non-limiting example, electrode 136 may detect and record electrical activity; for instance, but not limited to, the heart's electrical signals. In a non-limiting example, ultrasound sensor 132 may receive a set of sensor data 120 from electrode 136 incorporated with a catheter. For example, and without limitation, electrode 136 located at a tip of catheter may generate ultrasonic sound waves, from which ultrasound sensor 132 receives the ultrasonic waves and transmit a set of sensor data 120 related to the ultrasonic waves to processor 104. In some embodiments, ultrasound sensor 132 may include a transducer. For the purposes of this disclosure, a "transducer" is a component of an ultrasound sensor that converts one form of energy into another. In a non-limiting example, transducer may operate on a principle of piezoelectricity, where piezoelectric material can convert electrical energy into mechanical vibration (i.e. ultrasonic waves) and vice versa. In some cases, transducer may be arranged around a catheter tip or along its shaft. In a non-limiting example, the placement of transducers on a catheter may be arranged to capture detailed images of the surrounding tissues or organs. In some embodiments, ultrasound sensor 132 may include a transceiver. For the purposes of this disclosure, a "transceiver" is a combined unit of a transmitter and a receiver. In a non-limiting example, transceiver may transmit ultrasonic waves and receive echoes. In some cases, transceiver may be distributed along a catheter shaft or concentrated at specific locations of catheter. In a non-limiting example, the positioning of transceivers on a catheter may be determined by the type of data that transceivers need to communicate or sense. For example, and without limitation, in a cardiac catheter, transceivers may be placed to measure and transmit pressure data from within the heart. In some cases, ultrasound sensor 132 may sweep within organ as a part of refinement of organ model 112 to receive a set of sensor data 120. In a non-limiting example, ICE catheter placed within a heart may sweep within the heart to receive a set of sensor data 120. For example, and without limitation, ICE catheter or ultrasound sensor 132 may be moved manually by a user to sweep within an organ. For example, and without limitation, a probe of ICE catheter or ultrasound sensor 132 may rotate clockwise or counterclockwise to sweep within an organ. The refinement disclosed herein is further described below.

With continued reference to FIG. 1, for the purposes of this disclosure, "sensor data" is data received from a sensor. As a non-limiting example, sensor data 120 may include distance between sensor and surrounding tissue or organs. In a non-limiting example, sensor data 120 may include a plurality of distances between sensor and surrounding tissue or organ in different angles. For example, and without limitation, when ultrasound sensor 132 moves around (or sweep) within an organ, ultrasound sensor 132 receives a plurality of distances between ultrasound sensor 132 and organ and generate a set of sensor data 120 using the plurality of distances. As another non-limiting example, sensor data 120 may include signal strength or amplitude of ultrasonic signal emitted and received by ultrasound sensor 132, images within an organ, or the like. As another non-limiting example, sensor data 120 may include ambient temperature, humidity, atmospheric pressure, or the like. In some embodiments, sensor data 120 may be stored in model database 116. In some embodiments, sensor data 120 may be retrieved from model database 116. In some embodiments, user may manually input sensor data 120. In some embodiments, sensor data 120 may be received from remote device. As a non-limiting example, processor 104 may receive a set of sensor data 120 from a computing device or processor incorporated with ultrasound sensor 132.

With continued reference to FIG. 1, memory 108 contains instructions configuring processor 104 to determine an electrode position 140 within organ model 112 as a function of a set of sensor data 120 using a position machine-learning module 144. Position machine-learning module 144 disclosed herein may be consistent with a machine-learning module described with respect to FIG. 3. In a non-limiting example, position machine-learning module 144 may include a plurality of position machine-learning models as described below. Processor 104 is configured to determine a model position 148 within organ model 112 as a function of a set of sensor data 120. For the purposes of this disclosure, a "model position" is a specific spatial subset of an organ model. As a non-limiting example, model position 148 may include any part of an organ thereof. For example, and without limitation, model position 148 may include left ventricle, right ventricle, left atrium, right atrium, aorta, vena cava, or the like. For example, and without limitation, model position 148 may include left lobe, right lobe, inferior vena cava, segments I-VIII, or the like. In some embodiments, model position 148 may include 2D or 3D coordinates. In a non-limiting example, model position 148 may include any part of an organ where electrode 136 is located in. In a non-limiting example, processor 104 may determine model position 148 within organ model 112 as a function of set of images, ECG data, patient profile, or the like of a set of sensor data 120. For example, and without limitation, processor 104 may analyze a set of sensor data 120 that includes distances between ultrasound sensor 132 and organ obtained from various angles to determine model position 148 within organ model 112. In some embodiments, model position 148 may be stored in model database 116. In some embodiments, model position 148 may be retrieved from model database 116. In some embodiments, a user may manually input model position 148.

With continued reference to FIG. 1, in some embodiments, processor 104 may be configured to determine model position 148 using one position machine-learning model of position machine-learning module 144. In some embodiments, processor 104 may use position machine-learning module 144 to implement one or more algorithms or generate one or more position machine-learning models. In some embodiments, processor 104 may be configured to generate first position training data. In a non-limiting example, first position training data may include correlations between exemplary sensor data and exemplary model positions. For example, and without limitation, first position training data may include correlations between distances (sensor data 120) between ultrasound sensor 132 and organ and right atrium of a heart (model position 148). In some embodiments, first position training data may be stored in model database 116. In some embodiments, first position training data may be received from one or more users, model database 116, external computing devices, and/or previous iterations of processing. As a non-limiting example, first position training data may include instructions from a user, who may be an expert user, a past user in embodiments disclosed herein, or the like, which may be stored in memory and/or stored in model database 116, where the instructions may include labeling of training examples. In some embodiments, first position training data may be updated iteratively on a feedback loop. As a non-limiting example, processor 104 may update first position training data iteratively through a feedback loop as a function of sensor data 120, organ model 112, or the like. In some embodiments, processor 104 may be configured to generate first position machine-learning model of position machine-learning module 144. In a non-limiting example, generating first position machine-learning model may include training, retraining, or fine-tuning first position machine-learning model using first position training data or updated first position training data. In some embodiments, processor 104 may be configured to determine model position 148 within organ model 112 using first position machine-learning model (i.e. trained or updated first position machine-learning model). In some embodiments, generating training data and training machine-learning models may be simultaneous.

With continued reference to FIG. 1, processor 104 is configured to determine electrode position 140 within model position 148 of organ model 112 as a function of a set of-sensor data 120. For the purposes of this disclosure, an "electrode position" is the physical location or orientation of an electrode in a given space. In a non-limiting example, electrode position 140 may include a physical location or orientation of an electrode 136 within an organ or organ model 112. For example, and without limitation, electrode position 140 may include a physical location or orientation of an electrode 136 within model position 148 of organ or organ model 112. In a non-limiting example, electrode position 140 may include an orientation of electrode 136 in organ or organ model 112. In some embodiments, electrode position 140 may include 2D or 3D coordinates. In some embodiments, electrode position 140 may be stored in model database 116. In some embodiments, electrode position 140 may be retrieved from model database 116. In some embodiments, user may manually input electrode position 140.

With continued reference to FIG. 1, in some embodiments, processor 104 may be configured to determine electrode position 140 using one position machine-learning model of position machine-learning module 144. In some embodiments, processor 104 may use position machine-learning module 144 to implement one or more algorithms or generate one or more position machine-learning models. In some embodiments, processor 104 may be configured to generate second position training data. In a non-limiting example, second position training data may include correlations between exemplary sensor data and exemplary model positions. For example, and without limitation, second position training data may include correlations between distances (sensor data 120) between ultrasound sensor 132 and organ and coordinates of electrode position 140. In some embodiments, second position training data may be stored in model database 116. In some embodiments, second position training data may be received from one or more users, model database 116, external computing devices, and/or previous iterations of processing. As a non-limiting example, second position training data may include instructions from a user, who may be an expert user, a past user in embodiments disclosed herein, or the like, which may be stored in memory and/or stored in model database 116, where the instructions may include labeling of training examples. In some embodiments, second position training data may be updated iteratively on a feedback loop. As a non-limiting example, processor 104 may update second position training data iteratively through a feedback loop as a function of sensor data 120, organ model 112, an output of first position machine-learning model or any position machine-learning models of position machine-learning module 144, or the like. In some embodiments, processor 104 may be configured to generate second position machine-learning model of position machine-learning module 144. In a non-limiting example, generating second position machine-learning model may include training, retraining, or fine-tuning second position machine-learning model using second position training data or updated second position training data. In some embodiments, processor 104 may be configured to determine electrode position 140 within organ model 112 using second position machine-learning model (i.e. trained or updated second position machine-learning model). In some embodiments, generating training data and training machine-learning models may be simultaneous.

In a further embodiment, and still referring to FIG. 1, receiving set of sensor data 120 and determining electrode position 140 and model position 148 may involve one or more image preprocessing steps. In some cases, processor 104 may be configured to calibrate one or more ICE images of set of sensor data 120 by correct for distortions and ensure accurate spatial representation of cardiac anatomy pertaining to subject. In a non-limiting example, processor 104 may select one or more reference objects within ICE image that needs refinement to correct spatial distortions. In some cases, processor 104 may be configured to place a phantom with pre-determine dimensions in such ICE image and adjust ICE image until the phantom's dimensions are accurately represented. In another non-limiting example, one or more ICE images' brightness and contrast may be adjusted, by processor 104 to ensure that echogenicity (reflectivity) of the tissues is accurately represented. One or more tissues with known echogenicity may be selected by processor 104 as reference tissues to adjust corresponding portions of the one or more ICE images. In other cases, standardized correction curves may be applied in order to correct the echogenicity of ICE images. As an ordinary person skilled in the art, upon reviewing the entirety of this disclosure, may be aware of various refinement techniques, such as, without limitation, temporal refinement, geometric refinement, among others that can be used by processor 104 to preprocess set of sensor data 120.

Additionally, or alternatively, and still referring to FIG. 1, receiving set of sensor data 120 and determining electrode position 140 and model position 148 may include perform image segmentation on one or more ICE images of set of sensor data 120. In some cases, image segmentation may include separating specific structures or regions of interest (ROI) from the background or other structures in a given ICE image. In a non-limiting example, processor 104 may be configured to use edge detection algorithms to outline the heart chambers, separating them from surrounding tissues. One or more filters may be applied to highlight the boundaries between different types of tissues during the segmentation. In another non-limiting examples, valves and vessels may also be segmented by applying thresholding techniques. Processor 104 may be configured to set an intensity threshold based on the known echogenicity of blood and vessel walls and select pixels or regions having intensity below or above the intensity threshold from the given ICE image. In some cases, one or more machine learning models may be used to perform image segmentations, for example, and without limitation, a U-net (i.e., a convolution neural network containing a contracting path as an encoder and an expansive path as a decoder, wherein the encoder and the decoder forms a U-shaped structure).

processor 104 may generate a set of shape parameters based on set of images 112. As used in this disclosure, a "set of shape parameters" refers to a collection of numerical values or descriptors that quantitatively represent the geometric or morphological characteristics of a structure e.g., a heart. In a non-limiting example, set of shape parameters may include information and/or metadata calculated, determined, and/or extracted from set of ICE images, such as, dimensions, angles, curvatures, surface areas, texture, symmetry, and/or the like. In other embodiments, processor 104 may be configured to parameterize features (e.g., edges, textures, contours, and any other characteristics that describe the shape cardiac anatomy 116) extracted from set of images 112 using CNN described herein. Such parameterization may involve processor 104 to derive one or more shape parameters including one or more morphological descriptors that quantitatively describe cardiac anatomy 116 based on extracted features. In some cases, processor 104 may be configured to use principal component analysis (PCA) to reduce the dimensionality of set of shape parameters, allowing processor 104 to focusing on the most informative shape parameters of set of shape parameters in further processing steps described below.

With continued reference to FIG. 1, in a non-limiting example, set of shape parameters may be generated based on set of images 112 using machine learning model such as, without limitation, a shape identification model. Generating set of shape parameters may include receiving organ geometry training data, wherein the organ geometry training data may include a plurality of image sets or exemplary sensor data as input correlated to a plurality of shape parameter sets as output. In some cases, organ geometry training data may be received from model database 116 described herein. For example, and without limitation, organ geometry training data may be used to show each ICE image may indicate a particular set of shape parameters. Shape identification model may be trained, by processor 104, using organ geometry training data. Additionally, organ geometry training data may include previously input image sets and their corresponding shape parameters output. Shape identification model may be iterative such that outputs may be used as future inputs of shape identification model. This may allow the shape identification model to evolve. Processor 104 may be further configured to generate set of shape parameters as a function of set of images or sensor data 120 using the trained shape identification model.

With continued reference to FIG. 1, processor 104 may be configured to refine organ model 112 and generate a refined organ model 152 as a function of sensor data 120 and/or shape parameters. In a non-limiting embodiment, refining organ model 112 may include utilizing a statistical shape model (SSM). It should be noted that SSM may not be the only method for refining organ model 112. A person of ordinary skill in the art, upon reviewing the entirety of this disclosure, will be aware of various methods, such as, without limitation, mesh smoothing techniques, level set method, physics-based simulation, among others may be implemented, by processor 104, to refine organ model 112 described herein. As used in this disclosure, a "statistical shape model" is a data structure representing, including, and/or utilizing a mathematical model that captures principal modes of variation in shape across a population of organ anatomies. In some cases, SSM may be constructed by analyzing one or more datasets of shapes (sensor data 120) and identifying, for example, mean shapes and main modes of variation within the one or more datasets. In a non-limiting example, SSM may start with calculation of at least one mean shape, which represents an average geometry of all the organ shapes in a given dataset, wherein the at least one mean shape may be served as a central reference point for processor 104 to understand different variations. In some cases, dataset may include, without limitation, model training data, cardiac model training data, and/or any datasets within model database 116 described herein. SSM may also identify one or more principal modes of variation within given datasets described herein, wherein the "principal modes of variations," for the purpose of this disclosure, refer to main patterns or directions along which data points vary within dataset. In a non-limiting example, identifying principal modes of variations may include applying principal component analysis (PCA) on given dataset. Additionally, or alternatively, shapes may be described directly using plurality of shape parameter sets (in model training data, cardiac model training data, or the like). In some cases, shape parameter sets may correspond to a plurality of modes of variations. Further, one or more statistical constraints (e.g., mean, variance, correlation, boundary, proportion constraint and/or the like) may be introduced into SSM based on the distribution of shape parameters within plurality of shape parameter sets.

With continued reference to FIG. 1, refining organ model 112 may include aligning organ model 112 with 3D VOR of organ anatomy. In an embodiment, aligning organ model 112 with 3D VOR may include adjusting the position, orientation, and scale of organ model 112 to match the spatial distribution captured in 3D VOR. In some cases, matching organ model 112 to 3D VOR may include matching spatial features, wherein matching the spatial features may further include aligning the surface, boundaries and internal structures of organ model 112 with corresponding features in 3D VOR. In some embodiments, processor 104 may utilize one or more optimization techniques to achieve a desired alignment; for instance, and without limitation, processor may be configured to minimizing the difference between organ model 112 and 3D VOR using iterative closest point (ICP) algorithms, gradient descent, or any other optimization strategies. Additionally, alignment of organ model 112 with 3D VOR may also allow incorporation of patient-specific details (e.g., patient profile, sensor data 120, or the like) into organ model 112 to form a final model (refined organ model 152) as described in further detail below.

In a non-limiting example, and still referring to FIG. 1, refining organ model 112 may include deforming, using processor 104, organ model 112. As used in this disclosure, "deforming" means altering the geometric structure of a structure e.g., organ model 112 in a systematic and controlled manner to align the structure with the spatial characteristics captured in another structure e.g., 3D VOR. In some cases, processor 104 may utilize one or more mathematical deformation models such as, without limitation, B-splines, radial basis functions, or other deformation functions to control and guide the deformation process of organ model 112. In some cases, one or more constraints listed above may be applied, by processor 104, based on anatomical knowledge, biomechanical properties, or other relevant factors to ensure that the deformation of organ model 112 is realistic and consistent with physiological principles as would be understood and/or expected by an ordinary person skilled in the art.

Still referring to FIG. 1, additionally, or alternatively, refining organ model 112 may also include validating organ model 112 or deformed organ model against additional data such as, without limitation, expert input, adjust parameters, and/or the like. Such validation process may ensure that the refined organ model 152 accurately represents the underlaying anatomy of organ of a patient. In some cases, expert input may include any user input entered via a user interface. In a non-limiting example, expert input may include, without limitation, clinical assessment, anatomical knowledge, or other professional insights that guide and evaluate the refinement process inputted to apparatus 100 by one or more users including medical professionals, subjects, patients, and/or any other related individuals. In a further embodiment, validating organ model 112 or deformed organ model may also include fine-tuning defamation controls, alignment settings, or other model characteristics or properties to achieve desired alignment with 3D VOR or additional data. In some cases, other information that is incorporated and codified within organ model 112 or deformed organ model 112 such as medical imaging, biomechanical simulations, patient-specific data/metadata may be validated and cross-verified. At least a machine-learning process, for example a machine-learning model described herein, may be used to validate by processor 104. Processor 104 may use any machine-learning process described in this disclosure for this or any other functions.

With continued reference to FIG. 1, in some embodiments, embedded values described herein may be employed in the refinement process of organ model 112. In a non-limiting example, the embedded values may contribute to SSM by providing additional parameters that guide the deformation and alignment of the template to match 3D VOR. Embedded values such as, without limitation, model position 148 or electrode position 140 may be used by processor 104 to guide the deformation process by providing targets for alignment; for instance, and without limitation, SSM may be configured to identify specific target areas where organ model 112 that needs to be deformed. Model position 148, in this case, may reveal a bulge in organ wall that is not present in organ model 112. In some cases, sensor data 120 may define the exact shape of the bulge in LA wall. Processor 104 may then deform organ model 112, particularly the wall to match the bulge defined by sensor data 120 in 3D VOR.

With continued reference to FIG. 1, processor 104 may be configured to generate a refined organ model 152 as a function of refinement. As used in this disclosure, a "refined organ model" refers to an organ model customized to reflect a patient's organ. In an embodiment, refined organ model 152 may be derived from organ model 112 and adjusted based on sensor data 120. In such embodiment, refined organ model 152 may include a deformed organ model as described above. In a non-limiting example, 3D VOR may indicate a need of adjustment to organ model 112 to match subject's unique geometry. SSM may then be configured to generate refined organ model 152 that accurately captures such specific organ anatomy based on organ model 112 and 3D VOR. In other cases, organ model 112 may not need any refinement; for instance, and without limitation, if organ model 112 already align perfectly with subject's organ, no deformation or adjustment would be necessary, thereby resulting in refined organ model 152 that is identical to organ model 112.

Still referring to FIG. 1, in some cases, the refinement process may also include the incorporation of more detailed features and textures based on sensor data 120 thereof, enhancing the realism and specificity of organ model 112. In an embodiment, SSM may be integrated with one or more additional models such as, without limitation, texture models, appearance models, or functional models to generate refined organ model 152. In some cases, such integration may result in refined organ model 152 that reflects not just the geometry but also the biomechanical properties or blood flow dynamics within organ. In a non-limiting example, texture of the myocardium may be modeled, by integrating texture models with SSM, to represent the fibrous nature of the heart muscle. In another non-limiting example, appearance of blood vessels, including color variations and translucency, may be modeled, by integrating appearance models with SSM.

With continued reference to FIG. 1, alternatively, refining organ model 112 may include adjusting organ model 112 based on set of shape parameters. In an embodiment, processor 104 may be configured to map set of shape parameters to SSM. The mapping process may define how organ model 112 should be adjusted to represent specific subject's organ anatomy. In a non-limiting example, shape parameters may include one or more numeric values indicating a particular thick ventricular wall, processor 104 may configure SSM to adjust organ model 112 to reflect such characteristic. In an embodiment, generating refined organ model 152 may involve generating a 3D mesh or grid that accurately represents the shape defined by set of shape parameters; for instance, and without limitation, processor 104 may be configured to generate a 3D mesh for left ventricle with vertices and edges positioned according to specific curvature and thickness defined by set of shape parameters using SSM.

With continued reference to FIG. 1, in some embodiments, processor 104 may be configured to input refined organ model 152 back into model machine-learning module 124 and/or shape identification model for continuous learning. In some cases, training data for these models such as, without limitation, model training data, cardiac model training data, organ geometry training data, and/or the like may be updated, by replacing, appending or otherwise inserting refined organ model 152 (and corresponding set of ICE images) into the dataset. This iterative process may allow machine learning module to evolve over time, adapting to new set of ICE images and sensor data 120 and improving the accuracy of machine learning models generated by machine learning module. Incorporation of subsequent 3D models as additional training data may enable apparatus 100 to capture more variations and nuances in cardiac anatomy modeling, enhancing its ability to generalize across different patients and conditions.

Still referring to FIG. 1, additionally, processor 104 may use user feedback to train machine-learning models described above. For example, model machine-learning model and/or shape identification model may be trained using past inputs and outputs of model machine-learning model and/or shape identification model. In some embodiments, if user feedback indicates that a refine organ model 152 outputted by SSM was "bad," then that output and the corresponding input e.g., set of ICE images, corresponding organ model 112, may be removed from training data used to train model machine-learning model and/or shape identification model, and/or may be replaced with a value entered by, e.g., another user that represents an ideal 3D model of organ given the input the machine learning models originally received, permitting use in retraining, and adding to training data as described above; in either case, machine learning models described herein may be retrained with modified training data. In some embodiments, training data such as model training data and/or organ geometry training data may include user feedback. Further, apparatus 100 may be configured to validate one or more machine learning models described herein against real-world data, identifying areas where machine learning models may be underperforming or misaligned with clinical needs. Such feedback may also be used to guide model training, ensuring that machine learning models are not only accurate but also clinically meaningful and aligned with healthcare or medical professional's needs and priorities.

With continued reference to FIG. 1, memory 108 contains instructions configuring processor 104 to add a visual marker 156 onto electrode position 140 in model position 148 of organ model 112. For the purposes of this disclosure, "adding" an electrode position onto an organ model refers to the process of applying a visual marker onto an organ model at coordinates corresponding to an electrode position. In a non-limiting example, coordinates of organ model 112 may include embedded values of voxels. For the purposes of this disclosure, a "visual marker" is a symbol for orientation or identification of an electrode in an organ. As a non-limiting example, visual marker 156 may include an image, icon, text, visual detail of electrode 136, or the like. For example, and without limitation, processor 104 may add an image or any visual details of electrode 136 onto electrode position 140 in model position 148 of organ model 112. For example, and without limitation, processor 104 may add an icon representing electrode 136 onto electrode position 140 in model position 148 of organ model 112. For example, and without limitation, processor 104 may add texts that describes electrode position 140 of electrode 136 onto electrode position 140 in model position 148 of organ model 112. In some embodiments, user may manually add visual marker 156.

With continued reference to FIG. 1, in some embodiments, processor 104 may be configured to add visual marker 156 onto electrode position 140 in model position 148 of organ model 112 using one or more model generating algorithms. As a non-limiting example, one or more model generating algorithms may include procedural modeling, polygonal modeling, parametric modeling, volumetric modeling, point cloud modeling, procedural noise generation, deep learning-based algorithms, or the like. In a non-limiting example, processor 104 may add visual marker 156 onto electrode position 140 in model position 148 of organ model 112 using a deep neural network described in this disclosure. In some embodiments, processor 104 may transmit visual marker 156 added organ model 112 to a remote device to display it to user. For example, and without limitation, an image or any visual details of electrode 136 added onto electrode position 140 in model position 148 of organ model 112 may be displayed on remote device. For example, and without limitation, an icon representing electrode 136 added onto electrode position 140 in model position 148 of organ model 112 may be displayed on remote device. For example, and without limitation, texts that describes electrode position 140 of electrode 136 added onto electrode position 140 in model position 148 of organ model 112 may be displayed on remote device. For example, and without limitation, orientation of electrode 136 may be displayed on remote device using a wedge, an arrow, a cone showing the orientation of electrode 136, or the like. In an embodiment, remote device may include a display. For the purposes of this disclosure, a "display" is a device that presents visual information or data. As a non-limiting example, display may present visual information or data in one or more forms of text, graphics, images, video, animation, and the like. Display may be configured to provide a way for a user to view and/or interact with information, including but not limited to visual marker 156, organ model 112, and/or the like. In some embodiments, display may include different technologies, such as liquid crystal display (LCD,) a light-emitting diode (LED,) organic light-emitting diode (OLED,) plasma, projection, touch screen, and/or the like. In some embodiments, display may include varying resolutions, sizes, and aspect ratios.

Referring now to FIGS. 2A-D, exemplary embodiments of organ model 112 are illustrated. As shown in FIG. 2A, organ model 112 or refined organ model 152 may include a cardiac organ model 200. In other non-limiting example, organ model 112 or refined organ model 152 may include liver, pancreas, intestines, blood vessels organ model, or the like. Processor 104 may be configured to receive cardiac organ model 200. Processor 104 may be configured to determine model position 148 within cardiac organ model 200 as shown in FIG. 2B. Processor 104 may be configured to determine electrode position 140 and add visual marker 156 onto electrode position 140 in model position 148 of cardiac organ model as shown in FIG. 2C. In some embodiments, processor 104 may be configured to determine electrode position 140 and add visual marker 156 onto electrode position 140 in cardiac organ model as shown in FIG. 2D.

Figure 3:
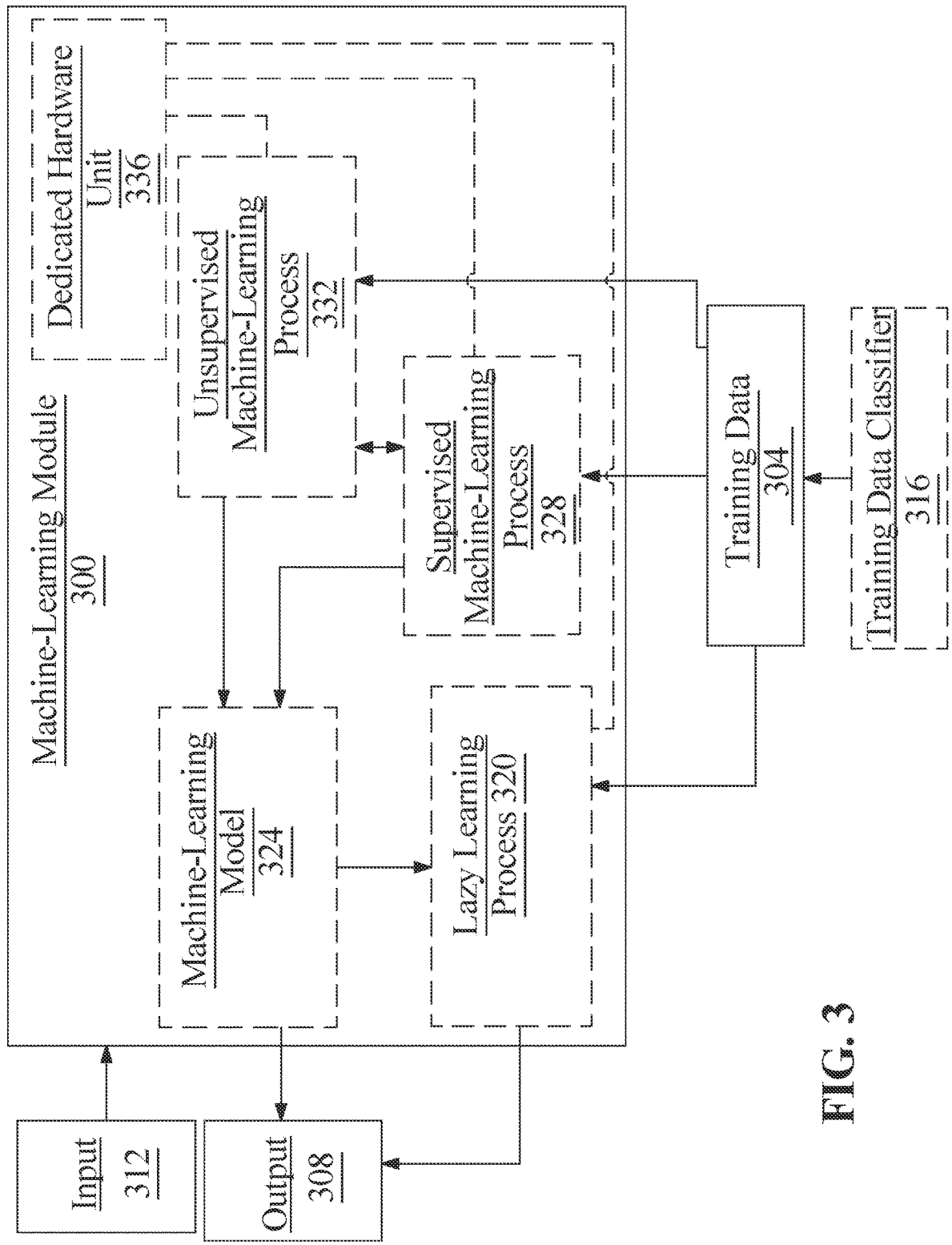
FIG. 3 illustrates a block diagram of an exemplary embodiment of a machine-learning module.

Referring now to FIG. 3, an exemplary embodiment of a machine-learning module 300 that may perform one or more machine-learning processes as described in this disclosure is illustrated. Machine-learning module may perform determinations, classification, and/or analysis steps, methods, processes, or the like as described in this disclosure using machine-learning processes. A "machine-learning process," as used in this disclosure, is a process that automatedly uses training data 304 to generate an algorithm instantiated in hardware or software logic, data structures, and/or functions that will be performed by a computing device/module to produce outputs 308 given data provided as inputs 312; this is in contrast to a non-machine-learning software program where the commands to be executed are determined in advance by a user and written in a programming language.

Still referring to FIG. 3, "training data," as used herein, is data containing correlations that a machine-learning process may use to model relationships between two or more categories of data elements. For instance, and without limitation, training data 304 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure. As a non-limiting illustrative example input data may include sensor data 120, patient profile, ECG data, or the like. As another non-limiting illustrative example output data may include electrode position 140, model position 148, organ model 112, or the like.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a data structure representing and/or using a mathematical model, neural net, or program generated by a machine-learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 300 may generate a classifier using a classification algorithm, defined as a processes whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to a cohort of patients or organs. For example, and without limitation, training data classifier 316 may classify elements of training data to patients' age, gender, or the like. For example, and without limitation, training data classifier 316 may classify elements of training data to different characteristics of organs such as heart, liver, pancreas, or the like.

Still referring to FIG. 3, computing device 304 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B) = P(B/A) P(A) = P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 304 may then calculate a likelihood table by calculating probabilities of different data entries and classification labels. Computing device 304 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 3, computing device 304 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 3, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm: , where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 3, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 3, computer, processor, and/or module may be configured to preprocess training data. "Preprocessing" training data, as used in this disclosure, is transforming training data from raw form to a format that can be used for training a machine-learning model. Preprocessing may include sanitizing, feature selection, feature scaling, data augmentation and the like.

Still referring to FIG. 3, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 3, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 3, computing device, processor, and/or module may be configured to precondition one or more training examples. For instance, and without limitation, where a machine-learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine-learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine-learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 3, computing device, processor, and/or module may down-sample elements of a training example to a desired lower number of data elements. As a non-limiting example, a high pixel count image may have 256 pixels, however a desired number of pixels may be 128. Processor may downsample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 3, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 3, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value has a minimum value in a set or subset of values subtracted therefrom, with the result divided by the range of the values, give maximum value in the set or subset: Feature scaling may include mean normalization, which involves use of a mean value of a set and/or subset of values, with maximum and minimum values: Feature scaling may include standardization, where a difference between and is divided by a standard deviation of a set or subset of values: . Scaling may be performed using a median value of a set or subset and/or interquartile range (IQR), which represents the difference between the $25^{th}$ percentile value and the $50^{th}$ percentile value (or closest values thereto by a rounding protocol), such as: Persons skilled in the art, upon reviewing the entirety of this disclosure, will be aware of various alternative or additional approaches that may be used for feature scaling.

Further referring to FIG. 3, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine-learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include sensor data 120, organ model 112, model position 148, electrode position 140, or the like as described above as inputs, organ model 112, model position 148, electrode position 140, or the like as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

With further reference to FIG. 3, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 3, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 3, machine-learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 332 may not require a response variable; unsupervised processes 332 may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 3, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAS, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 3, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 3, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 3, one or more processes or algorithms described above may be performed by at least a dedicated hardware unit 336. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 336 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 336 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 336 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 4:
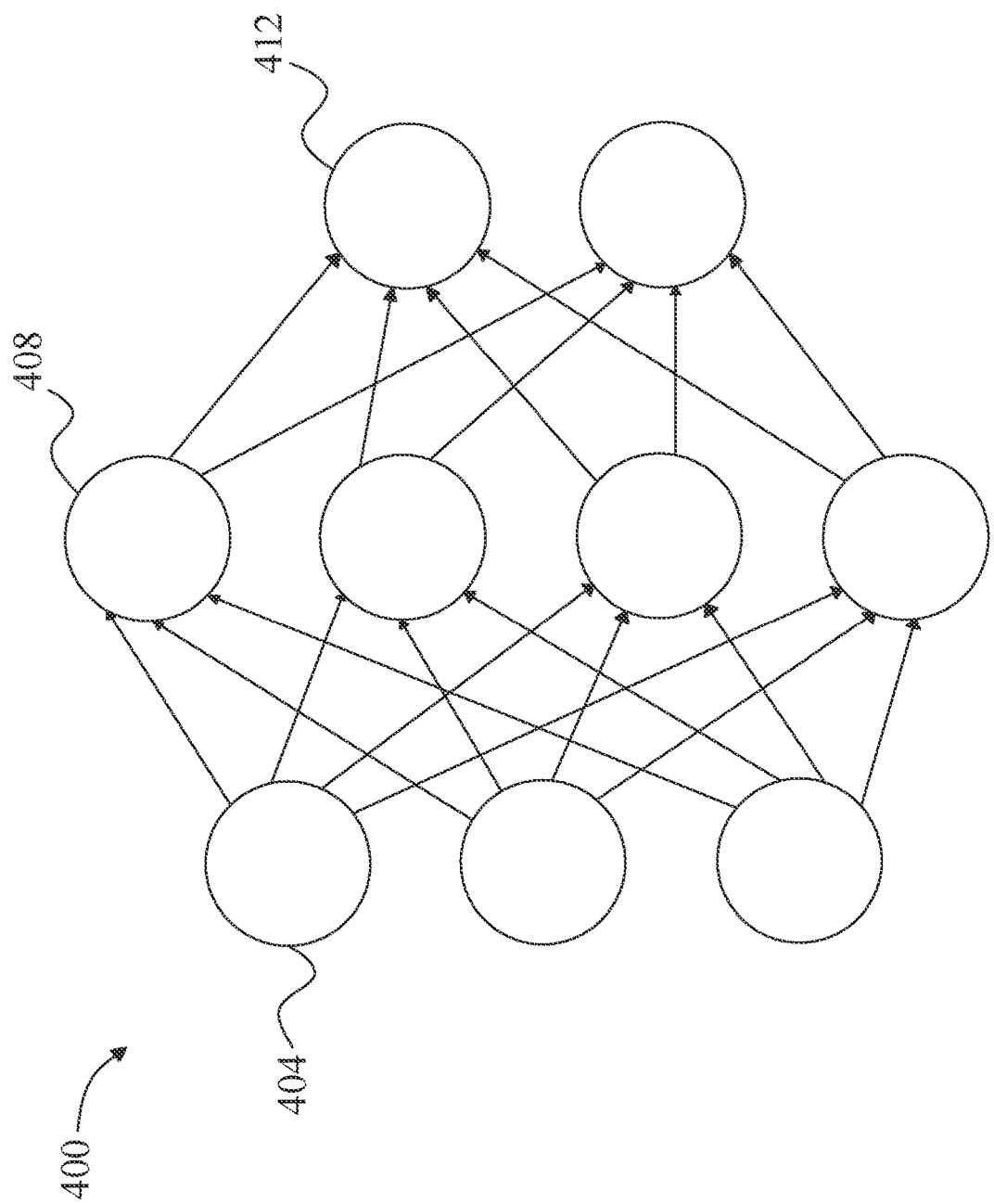
FIG. 4 illustrates a diagram of an exemplary neural network.

Referring now to FIG. 4, an exemplary embodiment of neural network 400 is illustrated. A neural network 400 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 404, one or more intermediate layers 408, and an output layer of nodes 412. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 5:
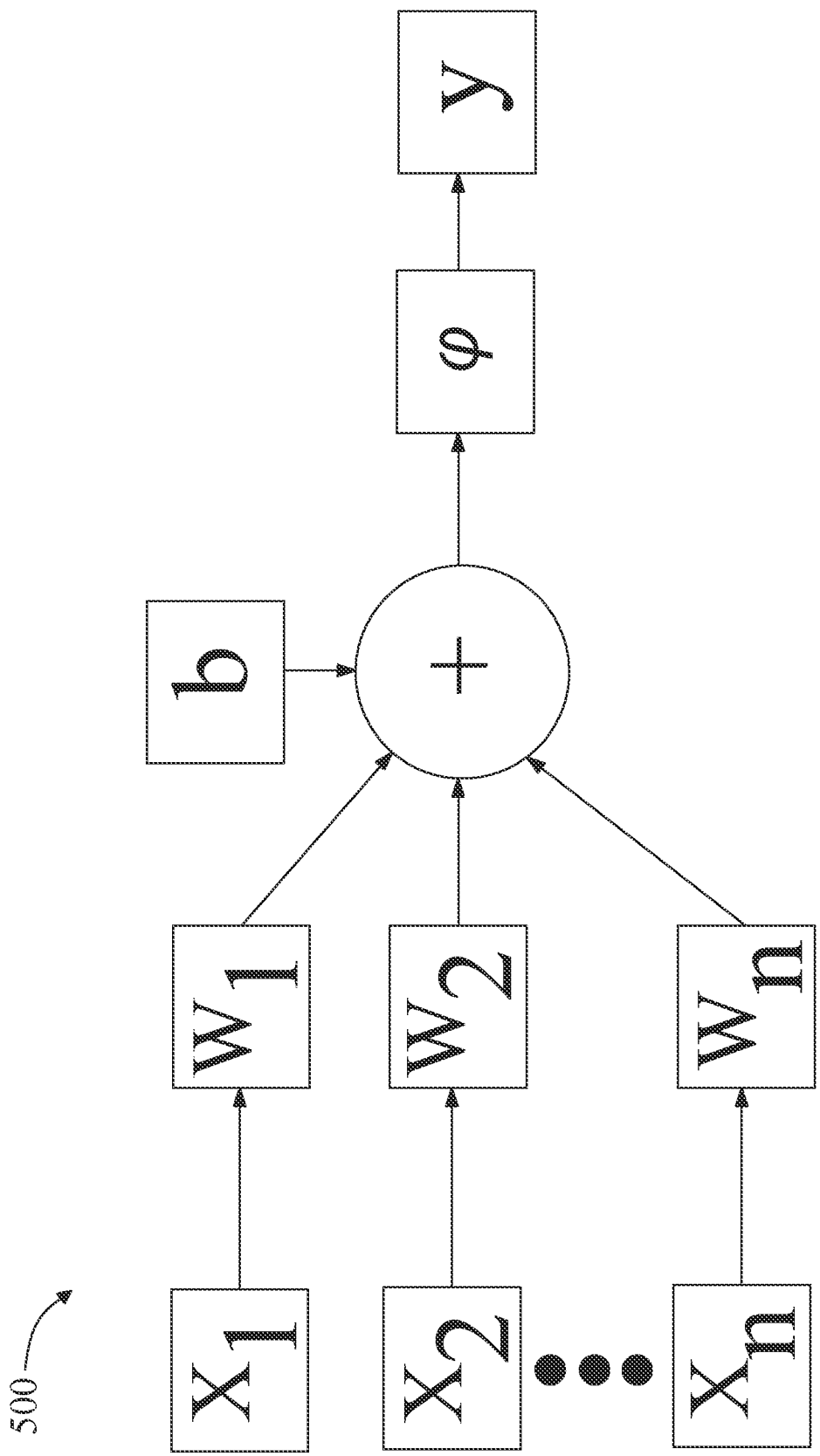
FIG. 5 illustrates a block diagram of an exemplary node of a neural network.

Referring now to FIG. 5, an exemplary embodiment of a node 500 of a neural network is illustrated. A node may include, without limitation, a plurality of inputs x; that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form given input x, a tanh (hyperbolic tangent) function, of the form, a tanh derivative function such as, a rectified linear unit function such as, a "leaky" and/or "parametric" rectified linear unit function such as for some a, an exponential linear units function such as for some value of (this function may be replaced and/or weighted by its own derivative in some embodiments), a softmax function such as where the inputs to an instant layer are, a swish function such as, a Gaussian error linear unit function such as $f(x)=$ for some values of a, b, and r, and/or a scaled exponential linear unit function such as. Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 6:
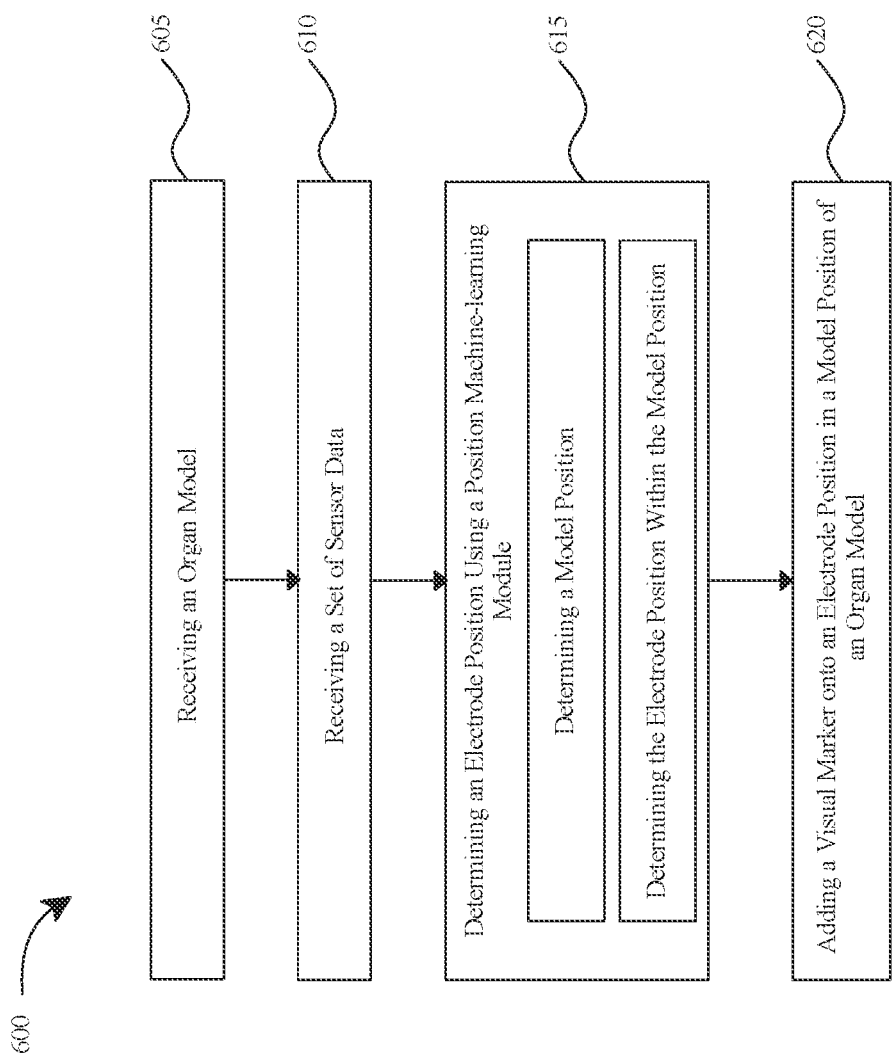
FIG. 6 illustrates a flow diagram of an exemplary method for locating position of an electrode on an organ model.

Referring now to FIG. 6, a flow diagram of an exemplary method 600 for locating a position of an electrode on an organ model is illustrated. Method 600 includes a step 605 of receiving, using at least a processor, an organ model, wherein the organ model is configured to digitally represent an organ. In some embodiments, method 600 may further include constructing, using the at least a processor, the organ model as a function of electrocardiogram data using a model machine-learning module. In some embodiments, method 600 may further include determining, using the at least a processor, a cardiac model machine-learning model from a plurality of model machine-learning models of the model machine-learning module as a function of the electrocardiogram data. These may be implemented as described with respect to FIGS. 1-5.

With continued reference to FIG. 6, method 600 includes a step 610 of receiving, using at least a processor, a set of sensor data from at least a sensor, wherein the at least a sensor includes an ultrasound sensor. In some embodiments, the ultrasound sensor may include an electrode. In some embodiments, the ultrasound sensor may include an intracardiac echocardiography (ICE) catheter configured to sweep within an organ to generate the set of sensor data as a part of refinement of the organ model. In some embodiments, method 600 may further include generating, using the at least a processor, a refined organ model as a function of the set of sensor data These may be implemented as described with respect to FIGS. 1-5.

With continued reference to FIG. 6, method 600 includes a step 615 of determining, using at least a processor, an electrode position within an organ model as a function of a set of sensor data using a position machine-learning module, wherein determining the electrode position includes determining a model position within the organ model as a function of the set of sensor data and determining the electrode position within the model position of the organ model as a function of the set of sensor data. In some embodiments, method 600 may further include generating, using the at least a processor, first position training data, wherein the first position training data may include correlations between exemplary sensor data and exemplary model positions, training, using the at least a processor, a first position machine-learning model of the position machine-learning module using the first position training data and determining, using the at least a processor, the model position within the organ model using the trained first position machine-learning model. In some embodiments, method 600 may further include generating, using the at least a processor, second position training data, wherein the second position training data may include correlations between exemplary sensor data and exemplary electrode positions, training, using the at least a processor, a second position machine-learning model of the position machine-learning module using the second position training data, wherein the second position training data may be iteratively updated on a feedback loop as a function of an output of a first position machine-learning model of the position machine-learning module and determining, using the at least a processor, the electrode position within the organ model using the trained second position machine-learning model. In some embodiments, the first position machine-learning model and the second position machine-learning model may include a deep neural network. These may be implemented as described with respect to FIGS. 1-5.

With continued reference to FIG. 6, method 600 includes a step 620 of adding, using at least a processor, a visual marker onto an electrode position in a model position of an organ model. In some embodiments, method 600 may further include transmitting, using the at least a processor, the visual marker added organ model to a remote device to display the visual marker added organ model to a user. These may be implemented as described with respect to FIGS. 1-5.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
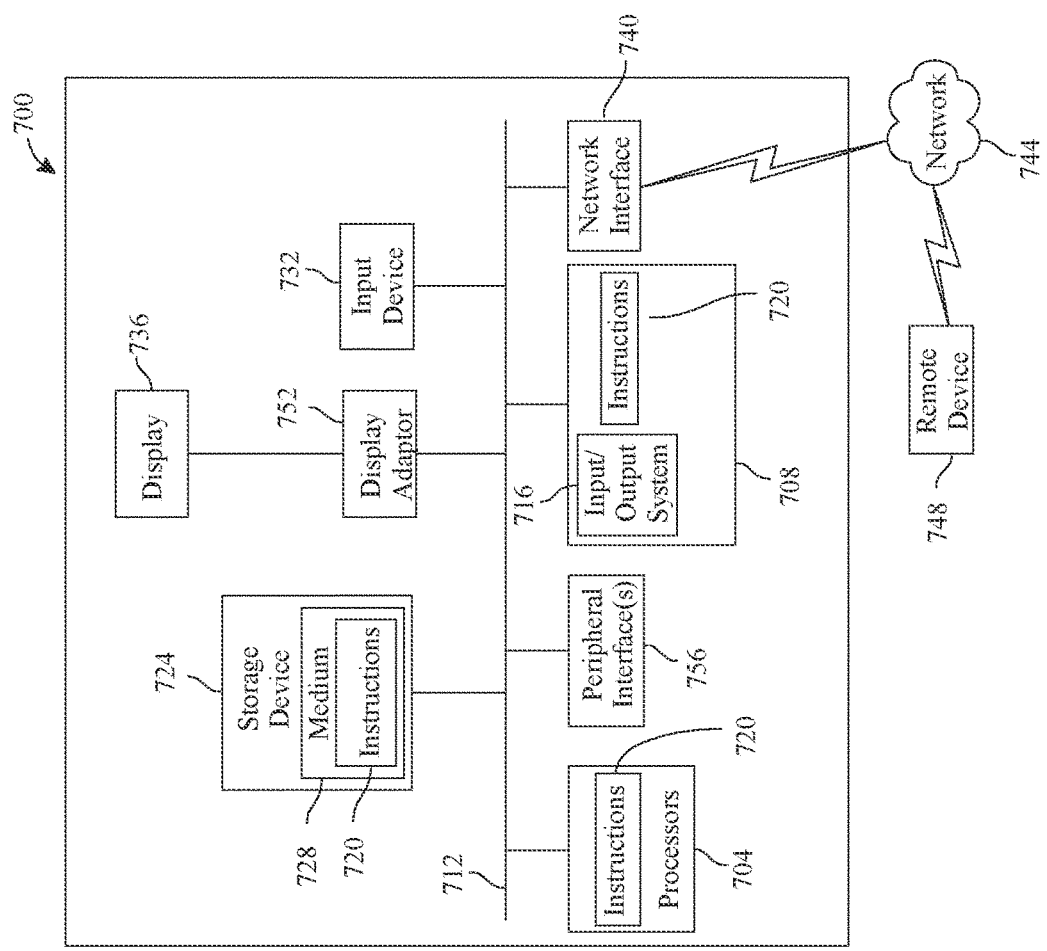
FIG. 7 illustrates a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and memory 708 that communicate with each other, and with other components, via a bus 712. Bus 712 may include any of several types of bus structures including, but not limited to, memory bus, memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a micro-controller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods and apparatuses according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for locating a position of an electrode on an organ model, the apparatus comprising:
at least a processor; and
a memory communicatively connected to the at least a processor, wherein the memory contains instructions configuring the at least a processor to:
receive an organ model, wherein the organ model is configured to digitally represent an organ;
receive a set of sensor data from at least a sensor, wherein the at least a sensor comprises an ultrasound sensor;
determine an electrode position within the organ model as a function of the set of sensor data using a position machine-learning module, wherein
determining the electrode position comprises:
determining a model position within the organ model as a function of the set of sensor data, wherein determining the model position further comprises:
generating first position training data, wherein the first position training data comprises correlations between exemplary sensor data and exemplary model positions;
training a first position machine-learning model of the position machine-learning module using the first position training data; and
determining the model position within the organ model using the trained first position machine-learning model; and
determining the electrode position within the model position of the organ model as a function of the set of sensor data, wherein determining the electrode position further comprises:
generating second position training data, wherein the second position training data comprises correlations between exemplary sensor data and exemplary electrode positions;
training a second position machine-learning model of the position machine-learning module using the second position training data, wherein the second position training data is iteratively updated on a feedback loop as a function of an output of the first position machine-learning model of the position machine-learning module; and
determining the electrode position within the organ model using the trained second position machine-learning model; and
add a visual marker onto the electrode position in the model position of the organ model.

2. The apparatus of claim 1, wherein the memory contains instructions further configuring the at least a processor to construct the organ model as a function of electrocardiogram data using a model machine-learning module.

3. The apparatus of claim 2, wherein the memory contains instructions further configuring the at least a processor to determine a cardiac model machine-learning model from a plurality of model machine-learning models of the model machine-learning module as a function of the electrocardiogram data.

4. The apparatus of claim 1, wherein the ultrasound sensor comprises an intracardiac echocardiography (ICE) catheter configured to sweep within the organ to generate the set of sensor data as a part of refinement of the organ model.

5. The apparatus of claim 1, wherein the memory contains instructions further configuring the at least a processor to generate a refined organ model as a function of the set of sensor data.

6. The apparatus of claim 1, wherein the ultrasound sensor comprises an electrode.

7. The apparatus of claim 1, wherein the first position machine-learning model and the second position machine-learning model comprise a deep neural network.

8. The apparatus of claim 1, wherein the memory contains instructions further configuring the at least a processor to transmit the visual marker added organ model to a remote device to display the visual marker added organ model to a user.

9. A method for locating a position of an electrode on an organ model, the method comprising:
  receiving, using at least a processor, an organ model, wherein the organ model is configured to digitally represent an organ;
  receiving, using the at least a processor, a set of sensor data from at least a sensor, wherein the at least a sensor comprises an ultrasound sensor;
  determining, using the at least a processor, an electrode position within the organ model as a function of the set of sensor data using a position machine-learning module, wherein determining the electrode position comprises:
    determining a model position within the organ model as a function of the set of sensor data, wherein determining the model position further comprises:
      generating first position training data, wherein the first position training data comprises correlations between exemplary sensor data and exemplary model positions;
      training a first position machine-learning model of the position machine-learning module using the first position training data; and
      determining the model position within the organ model using the trained first position machine-learning model; and
    determining the electrode position within the model position of the organ model as a function of the set of sensor data, wherein determining the electrode position further comprises:
      generating second position training data, wherein the second position training data comprises correlations between exemplary sensor data and exemplary electrode positions;
      training a second position machine-learning model of the position machine-learning module using the second position training data, wherein the second position training data is iteratively updated on a feedback loop as a function of an output of the first position machine-learning model of the position machine-learning module; and
      determining the electrode position within the organ model using the trained second position machine-learning model; and
  adding, using the at least a processor, a visual marker onto the electrode position in the model position of the organ model.

10. The method of claim 9, further comprising:
  constructing, using the at least a processor, the organ model as a function of electrocardiogram data using a model machine-learning module.

11. The method of claim 10, further comprising:
  determining, using the at least a processor, a cardiac model machine-learning model from a plurality of model machine-learning models of the model machine-learning module as a function of the electrocardiogram data.

12. The method of claim 9, wherein the ultrasound sensor comprises an intracardiac echocardiography (ICE) catheter configured to sweep within the organ to generate the set of sensor data as a part of refinement of the organ model.

13. The method of claim 9, further comprising:
  generating, using the at least a processor, a refined organ model as a function of the set of sensor data.

14. The method of claim 9, wherein the ultrasound sensor comprises an electrode.

15. The method of claim 9, wherein the first position machine-learning model and the second position machine-learning model comprise a deep neural network.

16. The method of claim 9, further comprising:
  transmitting, using the at least a processor, the visual marker added organ model to a remote device to display the visual marker added organ model to a user.

* * * * *